United States Patent [19]

Schulz et al.

[11] Patent Number: 5,162,212
[45] Date of Patent: Nov. 10, 1992

[54] TRANSAMINASE FROM E. COLI DH-1 (ATCC 33849)

[75] Inventors: Arno Schulz, Hattersheim; Klaus Bartsch, Steinbach; Dominique Tripier, Eppstein; Klaus Sauber, Bad Soden am Taunus, all of Fed. Rep. of Germany

[73] Assignee: Hoechst Aktiengesellschaft, Frankfurt am Main, Fed. Rep. of Germany

[21] Appl. No.: 854,516

[22] Filed: Mar. 20, 1992

Related U.S. Application Data

[62] Division of Ser. No. 359,591, Jun. 1, 1989.

[30] Foreign Application Priority Data

Jun. 3, 1988 [DE] Fed. Rep. of Germany ....... 3818851

[51] Int. Cl.$^5$ .................. C12P 13/00; C12P 7/40; C12N 9/10; C12N 1/00
[52] U.S. Cl. .................... 435/128; 435/136; 435/252.8; 435/193; 435/849
[58] Field of Search ............ 435/193, 849, 252.8, 435/128, 136

[56] References Cited

U.S. PATENT DOCUMENTS

| | | | |
|---|---|---|---|
| 4,525,454 | 6/1985 | Rozzell | 435/193 |
| 4,826,766 | 5/1989 | Rozzell | 435/193 |
| 4,859,591 | 8/1989 | Walter et al. | 435/193 |

FOREIGN PATENT DOCUMENTS

| | | |
|---|---|---|
| 0248357A2 | 12/1987 | European Pat. Off. |
| 0249188A2 | 12/1987 | European Pat. Off. |
| 0265852A2 | 5/1988 | European Pat. Off. |
| 0373597A2 | 6/1990 | European Pat. Off. |

OTHER PUBLICATIONS

Hanahan, J. Mol. Biol., 166:557–580 (1983).
The American Type Culture Collection Catalogue of Bacteria and Bacteriaphages, 17th Edition, p. 92 (1989).

*Primary Examiner*—David M. Naff
*Assistant Examiner*—Mike Meller
*Attorney, Agent, or Firm*—Finnegan, Henderson, Farabow, Garrett, and Dunner

[57] ABSTRACT

A new transaminase has been isolated from *E. coli* DH-1 (ATCC 33849). It is possible to use the transaminase with great efficiency to prepare L-phosphinothricin and gamma-aminobutyric acid from appropriate precursors by transferring an amino group from glutamate.

7 Claims, No Drawings

TRANSAMINASE FROM E. COLI DH-1 (ATCC 33849)

This is a division of application Ser. No. 07/359,591, filed Jun. 1, 1989.

DESCRIPTION

L-2-Amino-4-methylphosphinobutyric acid (called L-phosphinothricin or L-PPT hereinafter) or the salts thereof are—as has also been disclosed in German Offenlegungsschrift 29 39 269—the active components of the racemates which can easily be obtained chemically. The latter have, according to German Offenlegungsschrift 27 17 440, a very good and broad herbicidal activity against numerous monocotyledonous and dicotyledonous, annual and perennial weeds. Since L-PPT and the abovementioned derivatives thereof are about twice as active as the racemates, it was desirable to develop a process with which it is possible to make L-PPT available in larger amounts in a straightforward manner.

It has already been disclosed that L-PPT can be prepared by microbial biotransformation (EP 02 48 357). It is also mentioned in this patent application that E. coli DH-1 has transaminases which are able to convert the appropriate precursors into L-tert.-leucine and L-phosphinothricin.

It has now been found that E. coli DH-1 (ATCC 33849) synthesizes a specific transaminase which produces L-phosphinothricin with surprisingly high specificity.

Hence the invention relates to:
1. A transaminase from E. coli DH-1 having
   a molecular weight of 20,000 to 250,000 Dalton
   an isoelectric point at a pH between 3.0 and 8.0,
   a pH optimum in a range from 5.0 to 10.0 and
   a substrate specificity towards L-phosphinothricin, γ-aminobutyric acid and glutamate as amino-group donor as well as the appropriate keto compounds as amino-group acceptor.
2. A process for the preparation of the transaminase characterized under 1, which comprises cultivation of E. coli DH-1 and isolation of the said transaminase.
3. The use of the transaminase characterized under 1. for the transamination of (3-carboxy-3-oxo-propyl)-methyl-phosphinic acid to L-phosphinothricin and succinate semialdehyde to γ-aminobutyric acid.

The invention is described in detail hereinafter, especially in its preferred embodiments. The invention is furthermore defined in the patent claims.

The transaminase is isolated form E. coli DH-1 or from appropriate mutants or variants. For this purpose, the microorganism is cultivated in a nutrient medium optimal for the growth thereof. The microorganism is cultured aerobically, for example submerged with shaking or stirring in shaking flasks or fermenters, where appropriate introducing air or oxygen. The fermentation can be carried out in a temperature range of about 20° to 40° C., preferably at about 25° to 37° C., especially at 30° to 37° C. It is cultivated in a pH range between 5 and 8.5, preferably between 5.5 and 8.0. Under these conditions, the culture broth shows a considerable accumulation of the enzyme in general after 1 to 3 days. The synthesis of the transaminase starts in the middle of the log phase and reaches its maximum towards the end of the log phase. The production of the enzyme can be followed with the aid of activity assays by HPLC analysis or photometry.

The nutrient solution used to produce the transaminase contains 0.2 to 5%, preferably 0.5 to 2%, organic nitrogen compounds as well as inorganic salts. Suitable organic nitrogen compounds are: amino acids, peptones, also meat extracts, milled seeds, for example of corn, wheat, bean, soybean or the cotton plant, distillation residues from the production of alcohol, meat meals or yeast extracts. Examples of inorganic salts which the nutrient solution can contain are chlorides, carbonates, sulfates or phosphates of the alkali metals or alkaline earth metals, iron, zinc and manganese, as well as ammonium salts and nitrates.

The isolation and purification of the enzyme can be carried out by classical methods via lysozyme digestion, ammonium sulfate precipitation, and ion exchange and gel permeation chromatography.

The enzyme preparation can be characterized by a molecular weight of 20,000 to 250,000 Dalton, preferably 25,000 to 100,000, especially 40,000 to 50,000 Dalton, as well as by an isoelectric point which is at a pH of 3.0 to 8.0, preferably 3.5 to 5.5, especially 4.0 to 5.0. The pH optimum of the enzyme product is in the pH range 5.0 to 10.0, especially 8.0 to 9.0.

The first 33 N-terminal amino acids of the purified transaminase have been determined with the aid of a gas-phase sequencer and are: Met-Asn-Ser-Asn-Lys-Glu-Leu-Met-Gln-Arg-Arg-Ser-Gln-Ala-Ile-Pro-Arg-Gly-Val-Gly-Gln-Ile-His-Pro-Ile-Phe-Ala-Asp-Arg-Ala-Glu(Thr)-Asn-Asn(Gly).

This amino acid sequence shows no homology with transaminases previously disclosed in the literature.

The transaminase can be inhibited by the inhibitor O-(carboxymethyl)-hydroxylamine known from the literature, specifically under standard assay conditions (Example 3, enzyme activity) by 50% by about 0.1 to 1 μM O-(carboxymethyl)-hydroxylamine.

The investigations revealed that the enzyme is astonishingly stable at high temperatures. Thus, incubation of the enzyme at 70° C. for 10 minutes can be used in the enzyme purification to separate other proteins by thermal denaturation from the transaminase.

None of the 20 proteinogenous amino acids can be prepared with the aid of the transaminase according to the invention. Its only specificity is towards (3-carboxy-3-oxopropyl)-methylphosphinic acid as well as succinate semialdehyde and the esters thereof, from which the nonproteinogenous amino acids L-phosphinothricin and γ-aminobutyric acid can be prepared by transfer of the amino group from glutamate. Appropriate esters of keto acids which can be used are, in particular, lower alkyl ($C_1$–$C_6$) esters.

It is possible according to the invention for effective amounts of the transaminase to be used in free or immobilized form for the transamination. The known processes are suitable for the immobilization, such as the processes described in German Offenlegungsschriften 32 37 341 and 32 43 591. It has proven particularly advantageous in this connection to use a copolymer of vinyl acetate and divinylethylene-urea whose surface has been modified with oxirane groups after hydrolysis of the acetate groups. It is possible to couple the transaminase according to the invention with high efficiency to these oxirane groups. The enzyme coupled to the carrier material has proved to be very stable and showed almost no loss of enzymatic activity over a long period. It is advantageous to regenerate the enzyme as required with a small amount of about 5 μM pyridoxal phosphate.

The transamination reaction can be carried out in physiological buffer solutions, so that the enzyme activity is not adversely affected to a considerable extent, in a pH range of about 4 to 12, preferably in the range from pH 8 to pH 10. The reaction temperature can be varied in the range between 20° and 70° C. The rate of the enzyme reaction becomes increasingly slower at lower temperatures, while the enzyme is increasingly inactivated at higher temperatures. The enzyme reaction is carried out at a temperature of 20° to 60° C., preferably at 30° to 60° C., especially at 40° to 55° C.

Glutamate and the salts thereof are used as amino donor. It has proven beneficial for the reaction to use the amino donor in equimolar amounts or in an excess with respect to the α-keto acid or esters thereof. Ratios of 1:1 to 5:1, advantageously 1:1 to 2:1, have proven appropriate. The reaction components can be added to the reaction mixture as solution in water or by addition of the solid substances at the same time or continuously.

The product which is formed can be obtained from the reaction solution by known methods using ion exchange chromatography and spray drying.

The examples which follow serve to explain the invention further. Unless otherwise indicated, percentage data relate to weight.

EXAMPLE 1

Cultivation of *E. Coli* DH-1

To obtain the transaminase according to the invention, the bacterium *E. coli* DH-1 was cultured—as customary in microbiology—from a freeze-dried permanent form of the strain. Culturing took place initially in liquid, sterile complete medium. The growing bacteria were then streaked onto a solid nutrient medium in sterile Petri dishes, and single colonies were subsequently further cultivated in liquid medium.

| Liquid medium: | |
| --- | --- |
| Peptone from casein | 3.5 g/l |
| Peptone from meat | 3.5 g/l |
| Sodium chloride | 5.1 g/l |
| pH | 7.5 |
| Sterilization | 120° C., 20 minutes |
| Solid medium: | |
| Composition as liquid medium plus 15 g/l agar-agar. | |

The incubation of the bacteria to obtain the transaminase according to the invention was carried out in liquid medium in 5-liter Erlenmeyer flasks, each of which contained 1 liter of sterile medium, at 37° C. in a shaker at 200 revolutions per minute. Towards the end of the log growth phase the bacteria were harvested by centrifugation, deep-frozen in liquid nitrogen and stored at −80° C.

EXAMPLE 2

Isolation of the Transaminase from *E. coli* DH-1

The deep-frozen bacteria were suspended in twice the volume (2 ml/g of bacteria) of buffer A [20 mM phosphate buffer, 20 μM pyridoxal phosphate, 10 mM mercaptoethanol, (pH 7.0)] plus 1 mM phenylmethylsulfonyl fluoride (PMSF) and disrupted by ultrasound (15 min).

Cell detritus was removed by centrifugation, and the clear supernatant was fractionated by ammonium sulfate precipitation. The desired transaminase activity precipitated out of the solution between 40 and 70% ammonium sulfate saturation and was obtained by centrifugation, resuspended in buffer A and dialyzed against 50 times the volume of buffer A.

The dialysate was heated at 70° C. in the presence of 1 mM α-ketoglutarate for 10 min, and denatured proteins were removed by centrifugation. The clear supernatant was filtered through a 0.45 μm membrane and then loaded onto an anion exchanger composed of agarose with quaternary amino groups (Q-Sepharose HP®, Pharmacia) which was equilibrated with buffer A. Unbound proteins were removed by washing the column with buffer A, and bound proteins were eluted from the column with a linear gradient (0 to 1.0M KCl in buffer A) and collected in fractions. The transaminase was washed from the column at about 0.3M KCl.

The fractions with enzymatic activity were combined and, to reduce the volume, the protein was completely precipitated from the solution (80% ammonium sulfate saturation) and fractionated on a gel filtration column with a fractionation range of 10–400 kDalton (Ultrogel AcA 44, Serva). The buffer used for running the gel filtration was 20 mM piperazine-N,N'-(2-ethanesulfonic acid), 10 μM pyridoxal phosphate, 5 mM 2-mercaptoethanol, 0.1M KCl (pH 7.0). The fractions with enzymatic activity obtained after the gel filtration were dialyzed against 25 mM imidazole (pH 7.5), and the resulting proteins were fractionated according to their isoelectric points on Polybuffer Exchanger 94 (from Pharmacia) with Polybuffer 74 (Pharmacia). The transaminase according to the invention was eluted from the column at a pH of 4.35. The proteins in the fractions with enzymatic activity were completely precipitated from the solution (80% ammonium sulfate), dialyzed against buffer A and chromatographed on a high-resolution anion exchanger composed of agarose with quaternary amino groups (Mono Q, Pharmacia) (buffer system as described for Q-Sepharose HP). All foreign proteins have been removed from the transaminase after this purification step.

EXAMPLE 3

Characterization of the Enzyme

Molecular weight: about 44,000 Dalton (determined by polyacrylamide SDS gel electrophoresis).

Isoelectric point: pH 4.35 (determined by chromatofocusing on PBE 94/Polybuffer 74 from Pharmacia).

Enzyme activity: The enzyme activity was determined either by measuring the transamination of L-PPT in the presence of α-ketoglutarate as amino-group acceptor (assay 1) or by measurement of the production of L-PPT from (3-carboxy-3-oxo-propyl)methylphosphinic acid with glutamate as amino-group donor (assay 2). The results provided by the two assays were comparable so that, because the procedure was more straightforward, assay 1 was routinely used.

Assay 1: 10 mM PPT, 10 mM α-ketoglutarate in 100 mM tris-(hydroxymethyl)-aminomethane (tris)/10 μM pyridoxal phosphate (pH 7.5) were incubated at 30° C. for 30 minutes. The glutamate which was formed was determined by subsequent reaction with glutamate dehydrogenase as described in Methods in Enzymology, Vol. 113, pp. 245 et seq.

Assay 2: 10 mM (3-carboxy-3-oxo-propyl)-methylphosphinic acid, 10 mM glutamate, in place of PPT and α-ketoglutarate, otherwise as assay 1. The L-PPT which was formed was detected using an amino acid analyzer.

The specific enzyme activity of the purified protein was determined with these assays as 265 nkat/mg of protein (1 katal = 1 mole converted per second).

The pH optimum of the enzyme reaction measured in this way is about pH 9, and the temperature optimum is about 55° C.

The sequence of the first 40 N-terminal amino acids of the purified transaminase was determined in a gas-phase sequencer as follows: Met-Asn-Ser-Asn-Lys-Glu-Leu-Met-Gln-Arg-Arg-Ser-Gln-Ala-Ile-Pro-Arg-Gly-Val-Gly-Gln-Ile-His-Pro-Ile-Phe-Ala-Asp-Arg-Ala-Glu(thr)-Asn-Asn(Gly)-20.

EXAMPLE 4

Production of L-PPT with the Aid of the Purified Transaminase

The purified transaminase was incubated with a concentration of 0.1 mg/ml (specific enzyme activity 15 U/mg of protein) in 50 mM tris/10 μM pyridoxal phosphate (pH 9.0) with 30 g/l sodium (3-carboxy-3-oxo-propyl)-methylphosphinate and 60 g/l L-glutamate at 55° C. Samples were taken between 0 and 24 hours incubation time. After the sampling the enzyme was denatured at 95° C. for 10 min and removed by centrifugation, and the supernatants were examined in an amino acid analyzer for the formation of L-phosphinothricin. The conversion rates achieved in this were 16.6 g of L-PPT/l/h. This yield can also be distinctly improved by raising the enzyme concentration.

After the reaction was complete, 94.3% of the α-keto acid used had been converted into L-PPT (28.3 g/l).

EXAMPLE 5

Immobilization of the Transaminase

An enzyme fraction which had been partially purified as in Example 2 was used for the immobilization of the transaminase. About 20% of the total protein in this enzyme preparation was transaminase, and the enzyme activity was 76.4 nkat/ml (1 kat = 1 katal = 1 mole converted/second).

47 ml of this transaminase preparation in 1M potassium phosphate buffer (pH = 8.0) were added to 8 g of the polymeric carrier VA-Epoxy Biosynth ® from Riedel de Haën, and the mixture was rolled at room temperature for 2 days.

After washing with
1. 50 mM potassium phosphate buffer, pH 7.0,
2. 1M potassium phosphate buffer, pH 8.0 and
3. 50 mM potassium phosphate buffer, pH 7.0

31 g of wet resin were obtained.

Excess oxirane groups were converted by incubating the resin with 10 mM 2-mercaptoethanol (in 50 mM potassium phosphate buffer) for one hour.

The carrier resin had an enzymatic activity of 1,975 nkat after the coupling (64 nkat/g of wet resin) which corresponds to a coupling yield of 55%. Storage was in 50 mM potassium phosphate buffer, (pH 7.0) with 0.02% sodium azide at 4° C.

EXAMPLE 6

Production of L-PPT Using the Immobilized Transaminase

The coupled transaminase from Example 5 was used to produce L-PPT in a column reactor. For this purpose, a 20 ml chromatography column was packed with the immobilized transaminase, the column was equilibrated at 42° C., and substrate solution (20 g/l 3-carboxy-3-oxo-propyl-methylphosphinic acid (keto-PPT)/60 g/l L-glutamic acid/10 μM pyridoxal phosphate, pH 8.0) was pumped through the column at a flow rate of 0.5 ml/min. After passing through the column, 90.4% of the keto-PPT used had been converted into L-PPT.

We claim:

1. A purified transaminase from *E. coli* DH-1 (ATCC 33849) having
   a molecular weight of 20,000 to 250,000 Dalton,
   an isoelectric point at a pH between 3.0 and 8.0,
   a pH optimum in a range from 5.0 to 10.0, and
   a substrate specificity for transamination of (3-carboxy-3-oxo-propyl)-methyl-phosphinic acid or the esters thereof to produce L-phosphinothricin, and the transamination of succinic semialdehyde or the esters thereof to produce gamma-aminobutyric acid, with glutamate as amino-group donor.

2. The purified transaminase as claimed in claim 1, which has
   a molecular weight of 25,000 to 100,000 Dalton
   an isoelectric point at a pH between 3.5 and 5.5 and
   a pH optimum in a range 8.0 to 9.0.

3. A method for transamination comprising using a purified transaminase from *E. coli* DH-1 (ATCC 33849) having
   a molecular weight of 20,000 to 250,000 Dalton,
   an isoelectric point at a pH between 3.0 and 8.0,
   a pH optimum in a range from 5.0 to 10.0, and
   a substrate specificity to carry out transamination of (3-carboxy-3-oxo-propyl)-methyl-phosphinic acid of the esters thereof to produce L-phosphinothricin, and the transmination of succinic semialdehyde or the esters thereof to produce gamma-aminobutyric acid, with glutamate as amino-group donor.

4. The method as claimed in claim 3, wherein the transamination reaction is carried out at 20° to 60° C.

5. The method as claimed in claim 3, wherein the transamination reaction is carried out at a pH of 4 to 12.

6. The method as claimed in claim 3, wherein the transaminase is used in immobilized form.

7. The method as claimed in claim 6, wherein a copolymer of vinyl acetate and divinylethylene-urea is used as a carrier material to immobilize said transaminase.

* * * * *